United States Patent
Baltzersen et al.

(10) Patent No.: US 6,571,635 B1
(45) Date of Patent: Jun. 3, 2003

(54) METHOD AND ARRANGEMENT FOR INSPECTION OF BUOYANT OBJECTS

(76) Inventors: Øystein Baltzersen, Øvre Bakklandet, N-7013 Trondheim (NO); Sigbjørn Sangesland, Okstadbrinken 10, N-7075 Tiller (NO)

( * ) Notice: Subject to any disclaimer, the term of this patent is extended or adjusted under 35 U.S.C. 154(b) by 0 days.

(21) Appl. No.: 09/763,522

(22) PCT Filed: Sep. 2, 1999

(86) PCT No.: PCT/NO99/00274

§ 371 (c)(1), (2), (4) Date: Apr. 12, 2001

(87) PCT Pub. No.: WO00/14528

PCT Pub. Date: Mar. 16, 2000

(30) Foreign Application Priority Data

Sep. 3, 1998  (NO) ................................................ 984062

(51) Int. Cl.$^7$ ............................ G01N 29/26; B63B 59/00
(52) U.S. Cl. ............................. 73/625; 73/628; 114/222
(58) Field of Search .................... 73/620, 625, 622, 73/626, 627, 628; 114/222

(56) References Cited

U.S. PATENT DOCUMENTS

| 3,426,585 A | 2/1969 | Zemanek, Jr. et al. |
| 3,910,104 A | 10/1975 | Davies |
| 4,254,484 A | 3/1981 | Markowski et al. |
| 4,577,487 A | 3/1986 | Dooley |
| 4,784,078 A | * 11/1988 | Feurt .......................... 114/222 |
| 4,821,665 A | * 4/1989 | Matthias et al. ......... 114/221 A |
| 4,890,567 A | 1/1990 | Caduff |
| 5,047,990 A | 9/1991 | Gafos et al. |
| 5,691,474 A | 11/1997 | Gerz |
| 5,947,051 A | * 9/1999 | Geiger ....................... 114/222 |
| 6,003,377 A | * 12/1999 | Waag et al. ................ 702/171 |
| 6,317,387 B1 | * 11/2001 | D'Amaddio et al. ........ 114/222 |

FOREIGN PATENT DOCUMENTS

| EP | 352 117 | 1/1990 |
| NO | 179926 | 3/1994 |
| WO | WO 94/23311 | 10/1994 |

* cited by examiner

Primary Examiner—Helen Kwok
Assistant Examiner—Rose M. Miller
(74) Attorney, Agent, or Firm—Merchant & Gould P.C.

(57) ABSTRACT

The invention relates to a method and a device for determining the thickness and topography of buoyant objects, especially ship's hulls (1), by means of a beam (2, 17) carrying an array of ultrasound sensors (3). The object (1) and the beam (2) are moved relative to each other in the object's longitudinal direction while the distance between the object and the beam are automatically adjusted by raising/lowering the beam (2) by means of lifting means (6) and/or distance elements secured by floating bodies (4). The invention also relates to a device for implementing the method.

16 Claims, 3 Drawing Sheets

METHOD AND ARRANGEMENT FOR INSPECTION OF BUOYANT OBJECTS

The present invention relates to a method for detailed mapping of the thickness and topography of buoyant objects, especially ships' hulls, by means of a beam carrying an array of ultrasound sensors, together with a device for implementation of the method.

The term ultrasound sensor should be understood here to refer to a measuring device comprising means both for transmission of acoustic signals towards or into a structure, and means for measuring/recording acoustic signals reflected from the structure, possibly also means for processing the result of the measurement.

The invention is intended amongst other things for use in connection with inspection of a ship's bottom, as an objective evaluation of the state of the ship's hull with regard to corrosion. This is important in the context of classification approval, where there is a requirement for the surveying of corrosion with subsequent repairs according to certain criteria. By performing inspections regularly, or in good time before classification approval/repair, the shipowner obtains a sound decision basis for planning and selecting the most rational maintenance/repair measures.

Contact with a corrosive environment causes ships' bottoms to be exposed to internal corrosion. This applies particularly to tankers carrying crude oil, where a corrosive environment is created in the bottom of the tanks on account of the acid content of the crude oil, and water. For the main classification every 5 years, therefore, it is obligatory to inspect the ship for corrosion. During the inspection the thickness of the steel plates is measured both in order to check the strength of the hull and to prevent leaks due to pit corrosion. If the thickness falls short of the requirements stipulated by the classification society, the whole or parts of the steel plates concerned must be replaced.

The current traditional measuring method is based on manual spot measurements undertaken from the inside or occasionally by means of divers from the outside when the ship is in port. This method is not particularly suitable for internal inspection of oil tanks, since the tank has to be cleaned and ventilated before inspection, and this is a time-consuming procedure. Moreover, it can be difficult for the operator to gain access. In addition to this, more and more ships are equipped With a double bottom, thus making it difficult to inspect the outer hull.

Another problem with manual inspection methods is that they are dependent on the operator for choice of measuring point. There are procedures for preventing serious errors of choice, but full covering with an automatic measuring system in a fixed grid will always be better.

Another measuring method is described in NO-B-179, 926, where a small sensor array is employed mounted on a self-propelled vessel which scans the ship's bottom. The vessel is equipped with wheels, which provide a constant distance between the vessel and the ship's bottom. The position of the sensor array is measured continuously by means of a hydroacoustic positioning system, thus permitting the measurements to be assembled later to form a complete map of the ship's bottom. This method is based on movement and positioning of a small vessel which rolls on self-propelled wheels under the ship's hull, a procedure which requires complicated positioning equipment as well as being time and resource-demanding (an extra 24 hours in port for a vessel represents a substantial expenditure). Furthermore, powerful flow forces at the locations where the survey is conducted will also complicate the operation. Since the vessel is small, it is not possible to measure topography (dents, etc.) by this method. The method is specially developed for use in large oil tankers, and in addition it does not permit inspection of the curved transition between ship's bottom and ship's side (the apparent horizon).

U.S. Pat. No. 3,910,104 describes an apparatus and a method for ultrasonic testing of metal plates. The apparatus comprises a container filled with water and with an opening on the top, the object which has to be inspected being in contact with the water through the opening. Under the object and inside the container there is placed a beam equipped with an array of ultrasound sensors. The measuring is conducted by passing the object over the apparatus while the beam is moved backwards and forwards. The apparatus is intended for single plates and is not at all suitable for inspection of ships' hulls or large buoyant objects.

None of the said methods permit inspection of large objects such as, e.g., ships' hulls in a rapid and cost-effective manner. In particular the known methods fail to provide a fast and efficient mapping of the objects' topography and thickness.

The object of the invention is to solve the above-mentioned problems in the prior art by means of a method and a device which permit precise and rapid inspection of buoyant objects. This is achieved according to the invention by means of a beam carrying an array of ultrasound sensors, and by the object and the beam, which can be raised and lowered, and which extends along the whole or a substantial part of the width of the object, being moved relatively to each other in the object's longitudinal direction while the ultrasound sensors inspect the whole or a substantial part of the width of the object, thus permitting complete mapping to be achieved by means of one or a small number of passes relatively between the object and the beam.

The method and the device according to the invention are characterized by that which is set forth in the attached patent claims.

According to the prior art plate thickness and distance from the sensor can be calculated on the basis of each individual ultrasound measurement when the velocity of sound in the plate material and the water are known. Since the beam in a preferred embodiment assumes a known geometric shape (preferably a rectilinear shape), the shape of the object in a sectional plane through the beam can be mapped. In this manner the object's thickness and topography can be completely mapped by means of one or a small number of passes relatively between the object and the beam.

If the ultrasound sensors are placed in an articulated beam it may be appropriate to place an extra set of distance measuring devices in a straight line in order to measure distance/topography. Alternatively, each joint can have angle gauges for determining topography.

In a preferred embodiment of the method, the beam is stationary while the object is moved past the beam. In an embodiment of the device suitable for use in this method, the device comprises, means for determining the beam's position and prevent the beam's movement in the object's longitudinal direction, together with an adjustable securing device for restricting the beam's movement in its longitudinal direction (corresponding to the object's transverse direction). Thus the invention entails a complete mapping of the thickness of the whole or a substantial part of the object, the latter being drawn over a large array of ultrasound sensors. The sensors may be stationary or they may be arranged on a body which can be moved from one side of the beam to the other. When employed for determination of the thickness and topography of ships' hulls, the ship is moved across the beam under its own power, pulled by tugs, or by a winch while ultrasound sensors measure the plate thickness. While the ship is passing the beam, the measurements are assembled to form a detailed map of the thickness of the ship's flat bottom. The position of the measuring points in the latitudinal direction is given by the geometry of the equipment, while the position in the longitudinal direction is determined by, e.g. measuring wheels or other suitable positioning systems. The distance between the ship and the beam (depth setting) is adjusted by means of lifting means secured by floating bodies and/or securing means located on land. The device may be placed beside or in a lock, dock or at another practical location often passed by ships.

In a second embodiment of the invention, which is adapted to inspection of ships on the open sea, the floating body containing the beam consists of service boats equipped with position sensors for determining and controlling the relative movement between the beam and the ship.

In a further embodiment of the invention, which is adapted to use in connection with loading and unloading operations on a ship, the lifting means are secured by a service boat on the seaward side of the ship and a wagon on the quay side of the ship.

According to the invention the distance between the object and the beam is adjusted by moving the beam until it is located directly below the object.

As distance elements, fixed or rotating brushes, or high-pressure hose nozzles may also be employed, with the result that cleaning and inspection are performed in one operation while achieving optimal inspection distance in a simple manner.

The resolution along the beam will be given by the distance between the ultrasound sensors, e.g. 5 cm, while the resolution along the other axis (in the beam's transverse direction) is given by the ratio between the relative velocity and how often the measurements are logged. With modern distributed measuring and storing it is possible to attain a resolution of 5 cm along both axes at a relative velocity of, e.g., 0.25 m/s. The high resolution and the accurate positioning of the sensors on the beam permit control of a large number of measuring points with great accuracy. The measurements can subsequently be compared in order to establish the object's state of corrosion.

The invention also permits scanning of the transition between ship's bottom and ship's side together with the ship's side. For the part which is located above water a device may be employed which permits water contact between the sensor array and the ship's hull, each sensor, e.g., being provided with a jet of water which ensures the presence of a communication channel for ultrasound. A specially preferred embodiment of the invention for use in this connection comprises an "articulated" beam, i.e. a beam consisting of at least two parts interconnected by an articulated element, and where the parts can be pivoted in order to follow the contour of the object. The joint(s) may be of a type which offers limited angular alteration. For further adjustment of the distance between the beam and the ship's bottom/side, the beam may be provided with floating bodies and/or distance elements on or near the joint(s). The distance elements are also useful when employing a "rigid" (non-articulated) beam.

In the case of both a rigid and articulated beam it is important for the beam to be stable with regard to wave and flow forces, while at the same time keeping down the beam's weight. This is solved in a preferred embodiment by the beam consisting of a trusswork and being made of, e.g., steel, aluminium, titanium, or a fibre-reinforced composite material.

Due to the fact that the beam constitutes a fixed reference point along the whole or a substantial part of the object's width, the system also permits measurement of the topography (dents, etc.) of the ship's hull. This can be of great interest to insurance companies in connection with settlement of claims, and change of owner.

The method and device according to the invention will now be illustrated by means of non-limiting examples relating to determination of the thickness and topography of a ship's hull, and by means of the attached drawings, in which.

Figure 1:
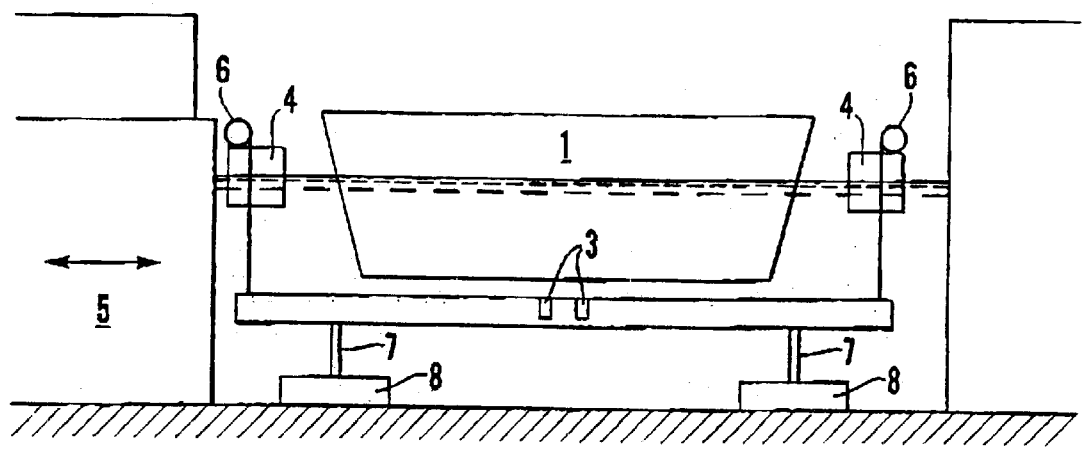
FIG. 1 is a front view of a first embodiment of the invention.
Figure 2:
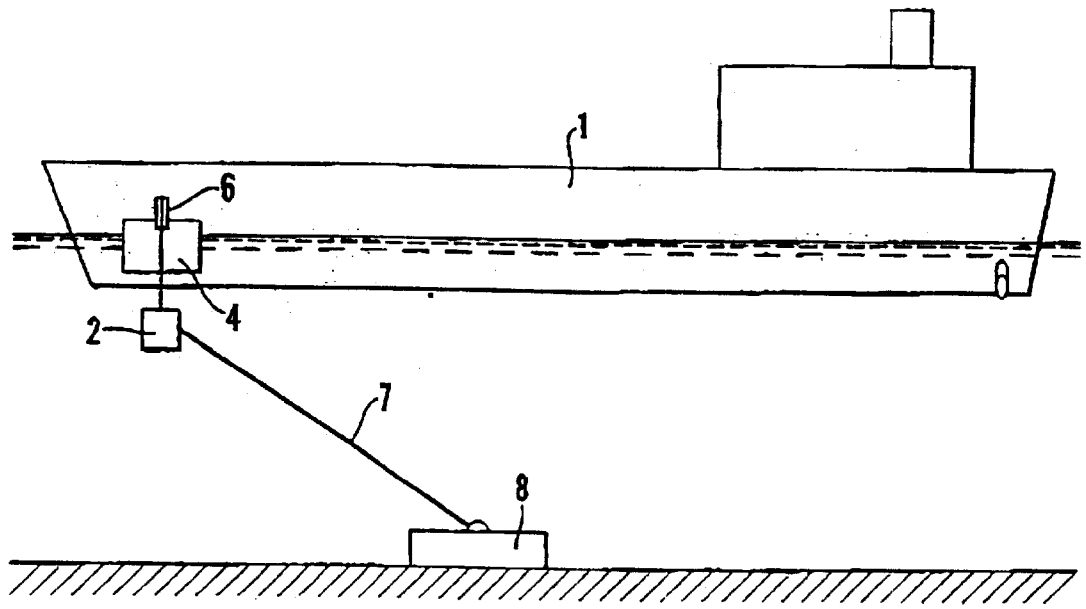
FIG. 2 is a side view of the same embodiment as that illustrated in FIG. 1.

FIGS. 1 and 2 illustrate a first embodiment of the invention. In this embodiment a beam 2 is provided with sensors 3 located under the ship 1 in a lock. Two buoyancy elements or floating bodies 4 are located on each side of the beam 2 which may be located directly behind the hatch or sliding door 5 in the lock. The beam's 2 vertical position is adjusted with respect to the draught of the ship 1 by means of a winch 6 located on each buoyancy element 4. The buoyancy elements 4 ensure that the distance between the beam 2 and the ship 1 remains constant even though the water level varies. The winch 6 may also be connected to attachment means on shore. In order to secure the beam 2 against horizontal movement due to hydrodynamic forces, an articulated securing device 7 or wire attached in foundations 8 on the bottom may be employed. As the ship 1 sails into or out of the lock, it moves over the beam 2 and the sensors 3 perform the mapping of thickness. After the ship 1 has sailed into the lock and the sliding door 5 behind the ship has been closed, the lock is drained or filled up to a new level before the foremost lock door is opened and the ship 1 continues on course. If there is room, the lock can accommodate several ships simultaneously.

When the system according to the invention is provided in a lock, it will be possible to implement scanning as the ship slides into or out of the lock. With a speed of 0.5 knots (0.25 m/sec), the scanning of a small tanker with a length of 150 m will be able to be conducted in the course of 10 minutes.

An alternative (not shown) to a lock is to employ a ship's dock (dry dock or floating dock). In this case relatively good control can be obtained of the ship's position, and the invention can be used for measuring the thickness and topography of the ship's hull.

Figure 3:
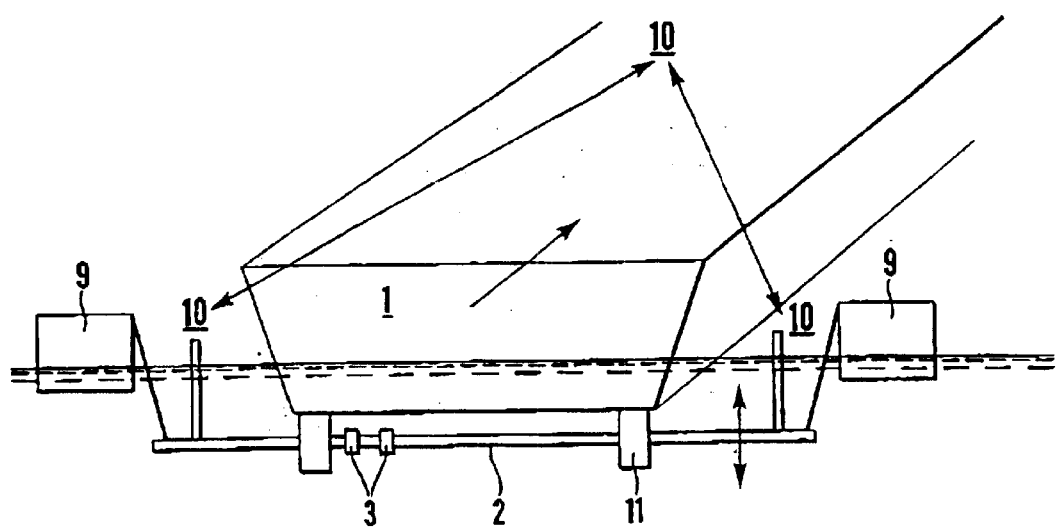
FIG. 3 is a front view of a second embodiment of the invention.

FIG. 3 illustrates a second embodiment of the invention, adapted for use on the open sea. In this case the beam 2 and the sensors 3 are kept at the correct distance from the ship 1 by means of two service vessels 9. For positioning of the beam 2 relative to the ship 1, use is made of a positioning system 10 suited to the purpose and distance elements 11. This embodiment of the invention places greater requirements with regard to positioning and greater requirements with regard to equipment and crew, but on the other hand it permits mapping of thickness on the open sea, e.g. of floating production ships, platforms or storage tanks which are not easy to move.

Figure 4:
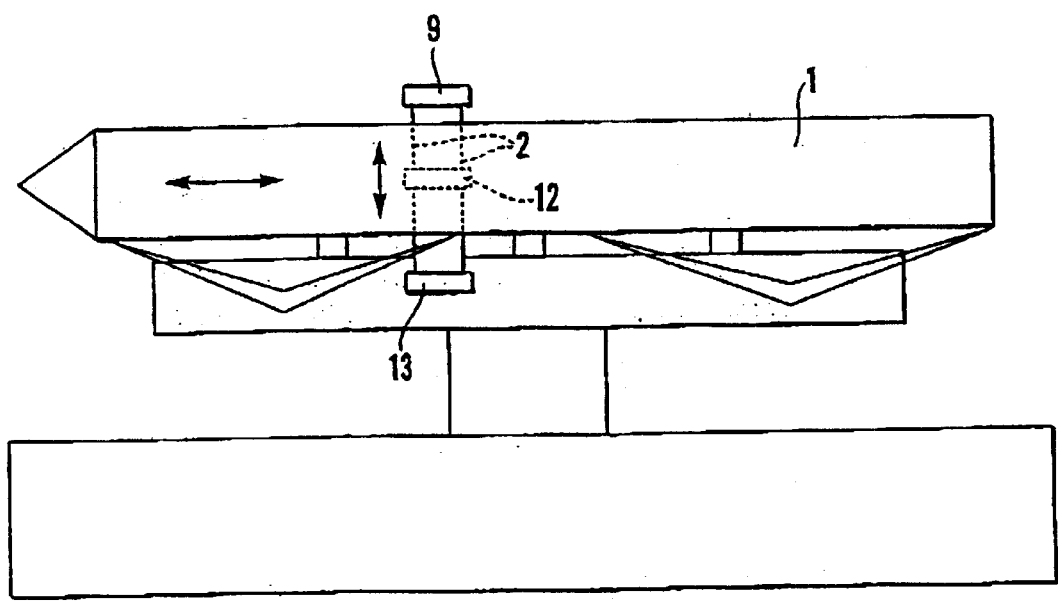
FIG. 4 is a view from above of a third embodiment of the invention.

FIG. 4 illustrates a third embodiment of the invention, adapted to use during loading/unloading of a ship 1. In this embodiment of the invention the beam 2 is provided with an elongate body 12 which is moved backwards and forwards on wires along the beam 2, thereby enabling the entire width of the ship to be mapped by a few sensors. The beam 2 is attached to a small service vessel 9 on the seaward side of the ship 1 and to a wagon 13 with a winch device on the quay side of the ship 1.

Figure 5:
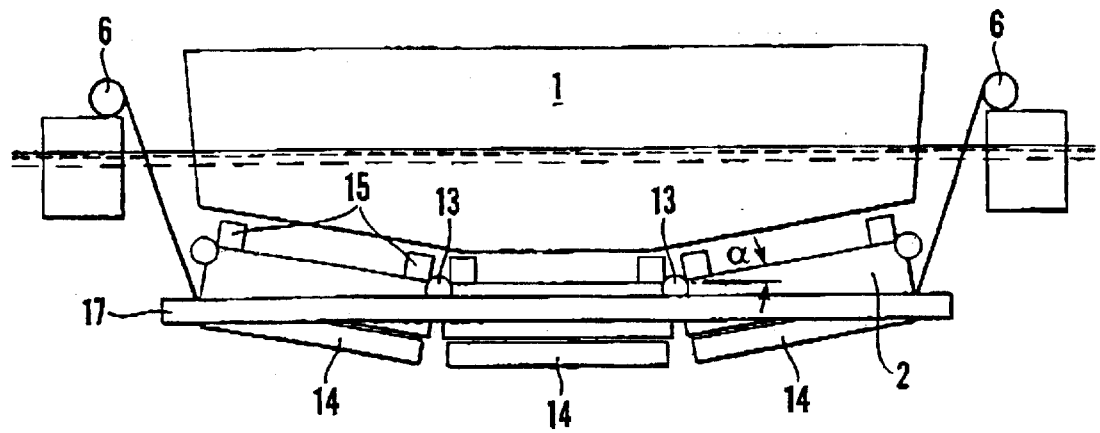
FIG. 5 is a front view of a first embodiment of an articulated beam.

FIG. 5 illustrates a first embodiment of an "articulated" beam 2. The beam 2 is provided with articulated elements 13 which permit parts of the beam to be pivoted in order to follow the contours of non-planar object, e.g. a ship's hull. In the figure the beam 2 is illustrated attached to winches 6, which are secured on land, but the use of the articulated beam is not thereby limited thereto. The beam 2 is also provided with floating bodies 14 and distance elements 15 whose function is to maintain the correct distance between the object and the beam. The device also comprises a rigid beam 17 or support structure, which is preferably straight, and where ultrasound sensors may be placed if desired in order to measure the distance to the ship's bottom or determine the topography of the bottom, while the bottom's thickness is measured by means of the articulated beam 2. The rigid beam 17 also acts as a stiffening structure. Another possibility is to omit the use of the rigid beam 17 and measure the angle α between the joints in the articulated beam 2.

In the illustrated embodiment the distance elements 15 consist of wheels, but they may also be provided in the form of runners. The distance elements may advantageously be employed in all embodiments of the invention, both together with an articulated beam and together with a non-articulated beam.

Figure 6:
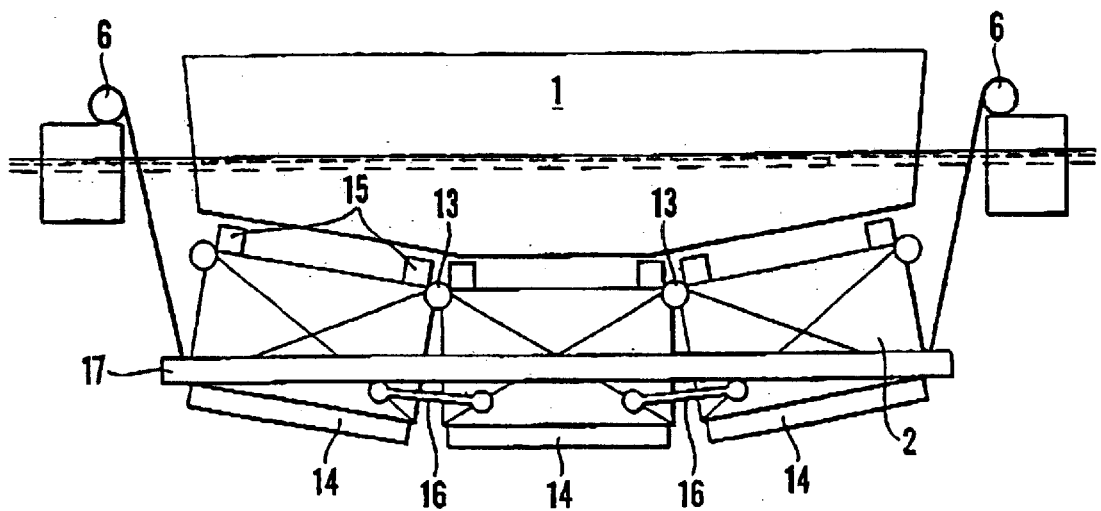
FIG. 6 is a front view of a second embodiment of an "articulated" beam.

FIG. 6 illustrates a second embodiment of an "articulated" beam 2. This beam 2 consists of a trusswork, the object of which is to make the beam stable relative to wave and flow forces. The beam 2 is also provided with articulated elements 13, floating bodies 14, distance elements 15 and also with spring elements 16 whose function is to ensure that all the distance elements 15 are in contact with the object. The floating bodies 14 may be employed as an alternative to the spring elements. In this case the device may also include a rigid beam 17 with the same function as that described in connection with FIG. 5. The spring elements 16 may also be employed in the embodiment illustrated in FIG. 5.

In the illustrated embodiments the beam extends substantially along the entire width of the object. In these cases mapping can be achieved by a simple relative pass between the object and the beam. An alternative is for the beam to extend only along a substantial part of the width of the object, for example substantially along half of the width of the object. In this case complete mapping can be achieved by means of a small number of, in this example two, passes relatively between the object and the beam. This assumes that the beam is displaced or moved between the passes, thus enabling different parts of the object to be mapped during each pass.

The system and the method according to the invention give the operator a more reliable basis for decisions concerning what kind of preventive maintenance should be implemented. It also offers the possibility of predicting the extent of possible repair requirements before the ship is brought into dock. The owners can thereby receive early clarification as to whether it is at all worth while repairing older ships.

What is claimed is:

1. A method for detailed mapping of thickness and topography of a buoyant object by means of a beam which is configured to be raised and lowered, said beam carrying an array of ultrasound sensors, wherein the object and the beam are moved in relation to each other while the ultrasound sensors inspect a part of a width of the object, the method comprising using the ultrasound sensors to inspect a whole or a substantial part of the width of the object, moving the object and the beam relative to each other in a longitudinal direction of the object, and adjusting a depth setting between the object and the beam by raising and lowering the beam by lifting means secured by floating bodies or by attachment means located on shore, thus permitting complete mapping to be achieved of the object's thickness and topography by means of one or a small number of passes between the object and the beam.

2. A method according to claim 1, wherein the depth setting between the object and the beam is adjusted automatically by raising and lowering of the beam by the lifting means, and that the beam constitutes a fixed distance reference along the whole or the substantial part of the width of the object, thus permitting measurement of topography, and that the fixed distance is provided by means of distance elements arranged on the beam.

3. A method according to claim 1, wherein a distance between the beam and the object is further regulated by the beam being divided or articulated into parts in order to follow the object's contour, and that determination of the object's thickness is performed by means of the sensors on the beam while determination of the object's topography is performed by measuring an angle between the beam's parts or by means of additional ultrasound sensors arranged on a rigid beam.

4. A method according to claim 1, wherein the beam is stationary and the object is moved past the beam.

5. A method according to claim 1, wherein the object is stationary and the beam is moved along the object.

6. A method according to claim 1, wherein the ultrasound sensors are arranged on a body which is moved backwards and forwards along the beam.

7. A method according to claim 1, wherein cleaning brushes or high pressure hosing are employed in a vicinity of the beam for cleaning the object before measurements are conducted.

8. A device for detailed mapping of the thickness and topography of a buoyant object, comprising a beam that is configured to be raised and lowered by lifting means, said beam carrying an array of ultrasound sensors, wherein the beam extends along a whole width of the object, wherein the ultrasound sensors are arranged to inspect a whole or a substantial part of the width of the object, wherein a position of the beam is fixed in a longitudinal direction of the object, and arranged for being passed by the object in the object's longitudinal direction, and wherein the lifting means are secured by floating bodies or by attachment means located on shore, thus enabling complete mapping of the object's thickness and topography to be achieved with one or a small number of passes between the object and the beam.

9. A device according to claim 8, wherein the lifting means are arranged for automatic depth setting of a distance between the object and the beam, and that the beam is provided with floating bodies and distance elements for automatic adjustment of the distance between the object and the beam, thus enabling the distance to be kept constant during mapping.

10. A device according to claim 8, wherein the beam consists of a trusswork.

11. A device according to claim 8, wherein the beam consists of at least two parts interconnected by means of an articulated element.

12. A device according to claims 9, wherein the distance elements include rotating brushes or high pressure hose nozzles in order to ensure an almost constant inspection distance over a whole extent of the beam while performing cleaning.

13. A device according to claim 8, wherein the sensors are evenly distributed and secured over the beam, or are arranged on a body which is movable from one side of the beam to the other.

14. A device according to claim 8, in which the beam is stationary and the object is moved past the beam, and wherein the device also comprises means for determining a position of the beam and preventing movement of the beam in a longitudinal direction of the object, together with an adjustable securing device for restricting the beam's movement in the longitudinal direction, corresponding to a transverse direction of the object, and that the securing device is located in a lock system or in a dock.

15. A device according to claim 9, wherein the device is adapted for use on open sea, the floating bodies including service boats equipped with sensors for determination and control of relative movement of the object and the sensors.

16. A device according claim 9, wherein the device is adapted for use in connection with loading and unloading operations, the lifting means being secured by a service boat on a seaward side of the object and a wagon on a quay side of the object.

* * * * *